(12) United States Patent
Tan et al.

(10) Patent No.: US 10,188,761 B2
(45) Date of Patent: Jan. 29, 2019

(54) GARMENT SANITIZER (71) Applicant: KONINKLIJKE PHILIPS N.V., Eindhoven (NL)

(72) Inventors: Boon Teck Tan, Eindhoven (NL); Kean Hao Raymond Lee, Eindhoven (NL); Bernd Laudahn, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 70 days.

(21) Appl. No.: 15/321,005

(22) PCT Filed: Jun. 30, 2015

(86) PCT No.: PCT/EP2015/064800
§ 371 (c)(1),
(2) Date: Dec. 21, 2016

(87) PCT Pub. No.: WO2016/001202
PCT Pub. Date: Jan. 7, 2016

(65) Prior Publication Data
US 2017/0151358 A1 Jun. 1, 2017

(30) Foreign Application Priority Data
Jun. 30, 2014 (EP) ..................................... 14174946

(51) Int. Cl.
*A61L 2/00* (2006.01)
*F26B 19/00* (2006.01)
*A61L 2/06* (2006.01)

(52) U.S. Cl.
CPC ............. *A61L 2/06* (2013.01); *A61L 2202/26* (2013.01)

(58) Field of Classification Search
CPC ............................... A61L 2/06; A61L 2202/26
(Continued)

(56) References Cited

U.S. PATENT DOCUMENTS

| 3,828,760 A | 8/1974 | Farber |
| 3,835,552 A | 9/1974 | Lord |

(Continued)

FOREIGN PATENT DOCUMENTS

| CN | 102907914 A | 2/2013 |
| GB | 210883 A | 2/1924 |

(Continued)

*Primary Examiner* — Monzer R Chorbaji (57) ABSTRACT

The invention relates to a garment sanitizing device (1, 31) comprising a housing (2), a chamber (4) within the housing to receive one or more garments (14) to be sanitized. The chamber (4) comprises a bottom wall, a top wall, and opposite first and second sides each extending from the bottom wall to the top wall. The housing contains a fan (6) and one or more heating elements (10). The at least one heating element is configured to directly heat garments within the chamber by radiation, and the fan is configured to convey air via the at least one heating element to heat the air and to convey the heated air through the chamber to additionally heat the garments by the conveyed heated air. The at least one heating element (10) is disposed proximate the first side of the chamber to heat garments (14) within the chamber from the first side of the chamber by radiation, and the garment sanitizing device is configured such that hot air heated by the at least one heating element is conveyed into the chamber from the second side of the chamber. The invention also relates to a corresponding method of sanitizing a garment.

15 Claims, 5 Drawing Sheets (58) Field of Classification Search
USPC .............................. 422/38, 307; 34/549, 553
See application file for complete search history.

(56) References Cited

U.S. PATENT DOCUMENTS

| | | |
|---|---|---|
| 3,858,331 A | 1/1975 | Lord |
| 5,870,836 A | 2/1999 | Grimes |
| 2010/0226821 A1 | 9/2010 | Ricciardi |
| 2013/0118023 A1 | 5/2013 | Cennon |

FOREIGN PATENT DOCUMENTS

| | | | | |
|---|---|---|---|---|
| WO | 9418839 A1 | 9/1994 | | |
| WO | 9622795 A1 | 8/1996 | | |
| WO | WO 96/22795 | * 8/1996 | .............. | A61L 2/06 |
| WO | 2006063569 A2 | 6/2006 | | |
| WO | 2007144432 A1 | 12/2007 | | |
| WO | 2012168897 A1 | 12/2012 | | |

* cited by examiner

FIG. 5 ize,
GARMENT SANITIZER

This application is the U.S. National Phase application under 35 U.S.C. § 371 of International Application No. PCT/EP2015/064800, filed on Jun. 30, 2015, which claims the benefit of International Application No. 14174946.5 filed on Jun. 30, 2014. These applications are hereby incorporated by reference herein.

FIELD OF THE INVENTION

The invention relates to the field of sanitizer devices and, more specifically, to a garment sanitizer.

BACKGROUND OF THE INVENTION

In the pursuit of maintaining a clean and hygienic domestic environment, various cleaning and sterilization appliances are available. Such devices include sterilizers for grooming utensils, tooth brushes, cooking utensils and infant feeding equipment. However, devices for hygienic sterilization of garments are less common.

Conventional washing machines do not typically reach the temperatures required to effectively sanitize clothing, meaning bacteria may survive the washing process and continue to grow on the garments. There are commercially available sterilizing washing machines that provide cold water with ozone. However such devices suffer the drawback that any remaining ozone residue may cause an environmental safety hazard if it escapes into the local environment. Washing machines are also available that provide a wash cycle capable of heating water up to around 95° C. However, a conventional domestic water supply, which typically contains a number of impurities, is not ideal for cleaning clothes even at high temperature. Such devices typically also consume a large volume of water and are of a bulky size.

WO 96/22795 A1 discloses a hot air sterilizer comprising a sterilizer chamber and a heat radiator subassembly disposed in the sterilizer chamber. The heat radiator subassembly comprises a heater and an impeller. Air is warmed up by the heater and the heated air is circulated by the impeller through the sterilizer chamber to sterilize appliances disposed in the sterilizer chamber.

GB 210 883 A discloses an apparatus for disinfecting clothes and WO 2006/063569 A2 discloses an apparatus for decontaminating temperature-sensitives objects.

SUMMARY OF THE INVENTION

It is an object of the invention to provide a garment sanitizer which substantially alleviates or overcomes one or more of the problems mentioned above.

The invention is defined by the independent claims; the dependent claims define advantageous embodiments.

According to the present invention, there is provided a garment sanitizing device comprising a housing, a chamber within the housing to receive one or more garments to be sanitized, the chamber comprising a bottom wall, a top wall, and opposite first and second sides each extending from the bottom wall to the top wall, the housing containing a fan and one or more heating elements, characterized in that the at least one heating element is configured to directly heat garments within the chamber by radiation, and the fan is configured to convey air via the at least one heating element to heat the air and to convey the heated air through the chamber to additionally heat the garments by the conveyed heated air, the at least one heating element being disposed proximate the first side of the chamber to heat garments within the chamber from the first side of the chamber by radiation, and the garment sanitizing device being configured such that hot air heated by the at least one heating element is conveyed into the chamber from the second side of the chamber. This advantageously enables heating and thereby sanitizing of garments both by radiation from a heater and by hot air, to aim to achieve thorough, efficient and quick garment sanitization. This advantageously ensures thorough and uniform garment sanitization, as the garments are heated from one side by radiation, and heated from the opposite side by the hot air from air flow guided into the chamber, so that the temperature through the garment is substantially consistent, and cool zones are avoided.

The garment sanitizing device may comprise at least one air flow passage configured to guide the flow of heated air from the fan. This advantageously helps to make the airflow through the device most efficient.

The chamber may comprise a plurality of walls and the housing may comprise a plurality of panels, and the chamber may be disposed within the housing such that the chamber walls are spaced from the housing panels such that at least one air flow passage is defined between the chamber walls and the housing panels, and the garment sanitizing device may be configured such that air is circulated by the fan from the chamber, through the air flow passage and back into the chamber. This advantageously provides a space-efficient construction to include sufficient air flow passages whilst allowing maximum space for garments within the chamber.

The fan may be disposed in a space defined between the chamber walls and housing panels. This advantageously provides a most space-efficient location for the fan, whilst allowing overall appliance size to be kept to a minimum.

The chamber may include a first wall on the first side of the chamber which comprises a plurality of apertures through which air may pass when being circulated by the fan. This advantageously allows airflow through the first wall to allow circulation of the heated air.

The chamber may include a second wall on the second side of the chamber opposite to the first side, and the second wall may include a plurality of apertures through which air may pass when being circulated by the fan.

At least one heating element may be provided proximate the first wall of the chamber.

The first wall may comprise a rear wall of the chamber, and the second wall may comprise a front wall of the chamber. Alternatively, the first and second walls may respectively comprise front and rear walls of the chamber. In a further alternative arrangement, the first wall may comprise a side wall of the chamber, and the second wall may comprise an opposite side wall of the chamber.

The garment sanitizing device may include an airflow guide to guide air from the air flow passage into the chamber. The airflow guide may be disposed on a panel of the housing. The airflow guide may project from proximate a central portion of the panel of the housing. The airflow guide may be configured to create a turbulent flow of hot air within the chamber. The air flow guide advantageously ensures continuous air flow through the chamber with minimum loss of air flow speed. Creating turbulence aids the air flow to surround and permeate the garments for optimum sanitizing effect.

At least one shelf may be provided within the chamber to receive garments to be sanitized, and the garment sanitizing device may be configured to convey the heated air through the chamber and over, under and around the shelf in a direction parallel to the plane of the shelf. This advantageously encourages the heated air to flow between and/or permeate between the garments stacked on the shelf to help towards achieving uniform and complete sanitization of all garments within the chamber.

The garment sanitizing device may comprise a single heating element configured to heat garments within the chamber by radiation and also configured to heat air conveyed through the chamber by the fan. This advantageously provides an efficient and space-saving configuration by a single heater providing both air-heating and garment-heating functions.

A control system may be provided to control operation of the garment sanitizing device. The control system may include a control unit having a user interface and a display screen. The control system may comprise a controller having a processor and a memory unit. Various different operating cycles of the garment sanitizing device may be stored in the memory unit.

The control system may be configured to control operation of the garment sanitizing device for a predetermined period of time, which may comprise between 15 minutes to 3 hours. The operating time may be determined and input by a user using the user interface. The controller may be configured to control and alter the operation of the garment sanitizing device, for example the operating temperature, time and/or air flow rate through the chamber, in dependence on the number of garments within the chamber. The number of garments within the chamber may be manually input by a user using the user interface, or by detection by an appropriate sensor, as described below.

The control system may be configured to allow remote control of the garment sanitizing device and may include a remote control transmitter to send control signals to affect operation of the garment sanitizing device. The garment sanitizing device may be configured to be controlled remotely by a mobile phone, such as with a mobile phone with a specific app loaded on the phone. All such control features advantageously provide ease of operation for a user.

The garment sanitizing device may comprise one or more sensors to detect one or more parameters within the garment sanitizing device and/or the chamber, and operation of the garment sanitizing device may be controlled in dependence upon signals received from the sensor(s).

The or each sensor may be configured to determine the number of garments within the garment sanitizing device and/or the required work load of the garment sanitizing device, and the control system may be configured to control the fan speed in dependence on the signal(s) received from the or each sensor. The control system may be configured to control the heater output in dependence on the signal(s) received from the or each sensor. One sensor may comprise a temperature sensor. The temperature sensor may be connected to the controller so that operation of the garment sanitizing device may be controlled so that the temperature within the chamber, as detected by the temperature sensor, is maintained at a predetermined temperature, and operation of the heater controlled in dependence on the detected temperature to remain at or around the predetermined temperature. The temperature may be selected by a user, and may be within a predetermined range of temperatures, which may be between 50 to 120 degrees Celsius. This advantageously allows a uniform temperature to be maintained in the chamber, and helps towards ensuring sufficient temperature for effective sanitization of garments whilst avoiding excessive temperature which could damage garments.

The garment sanitizing device may additionally, or alternatively, comprise a weight sensor to detect the weight of garments within the chamber to be sanitized. Such sensor may be mounted on a shelf or bottom surface of the chamber upon which garments to be sanitized may be stacked. The weight sensor may be connected to the controller so that operation of the garment sanitizing device may be controlled in dependence on the detected weight of garments, for example, operating cycle duration or temperature. This advantageously helps determine the amount and/or mass of clothes within the garment sanitizing device such that the device can be operated for a sufficient time for thorough sanitization of the garments.

The garment sanitizing device may additionally, or alternatively, comprise an airflow sensor to detect the flow rate and/or speed of air flowing through the chamber. The airflow sensor may be connected to the controller to maintain air flow rate or speed through the chamber at or around a predetermined value. This advantageously determines the speed of air being circulated by the fan through the chamber and the controller may control the fan speed to maintain a pre-set or pre-determined speed/flow rate. For example, if large amount of garments are placed in the chamber, the fan speed may need to be increased to maintain airflow around the large obstacle at a desired rate.

The garment sanitizing device may additionally, or alternatively, comprise a height sensor to determine the height of a stack of garments within the chamber. The height sensor may be connected to the controller so that operation of the garment sanitizing device may be controlled in dependence upon signals from the height sensor. For example, if the fan speed and/or heater output may be controlled in dependence upon the height of garment stacked within the chamber, as detected by the height sensor. This advantageously enables operation of the garment sanitizing device to be controlled effectively and efficiently in dependence on the number of garments within the chamber to be sanitized.

The present invention also provides a method of sanitizing a garment using a garment sanitizing device comprising a housing, a chamber within the housing to receive one or more garments to be sanitized, the chamber comprising a bottom wall, a top wall, and opposite first and second sides each extending from the bottom wall to the top wall, the housing containing a fan and one or more heating elements, the at least one heating element being disposed proximate the first side of the chamber, the method comprising placing garments within the chamber, directly heating the garments within the chamber from the first side of the chamber by radiation from the at least one heating element, and additionally heating the garments using heated air by activating the fan to convey air via the at least one heating element to heat the air and to convey the heated air through the chamber from the second side of the chamber to heat the garments.

The chamber may comprise opposite first and second sides, and the method may comprise heating garments by radiation from the first side of the chamber by at least one heating element disposed proximate the first side of the chamber, and heating the garments using heated air conveyed into the chamber from the second side of the chamber.

The garment sanitizing device may include one or more sensors connected to the controller to detect one or more parameters within garment sanitizing device and/or the chamber. The method may include receiving signals from a sensor within the chamber and controlling operation of the garment sanitizing device in dependence on the received signals. The method may include controlling operation of the garment sanitizing device in dependence on one or more of a temperature signal, weight signal, height signal and/or air flow signal received from the or each sensor.

The garment sanitizing device may comprise an airflow guide, and the method may comprise passing the airflow over the airflow guide and thereby guiding the airflow into the chamber. The method may comprise changing the direction of airflow by substantially 90 degrees using the airflow guide.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
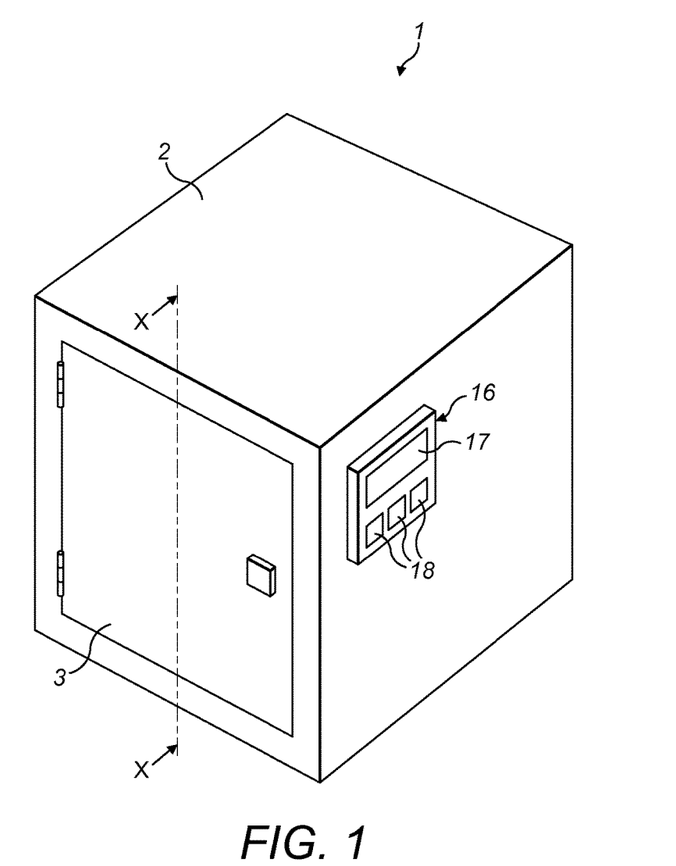
FIG. 1 shows a perspective view of a garment sanitizer of a first embodiment of the invention.

FIG. 1 shows a garment sanitizer 1 of a first embodiment of the invention which comprises a generally parallelepiped housing 2 having a plurality of panels and one panel comprises a door 3 to allow a user to access the interior of the housing 2.

Figure 2:
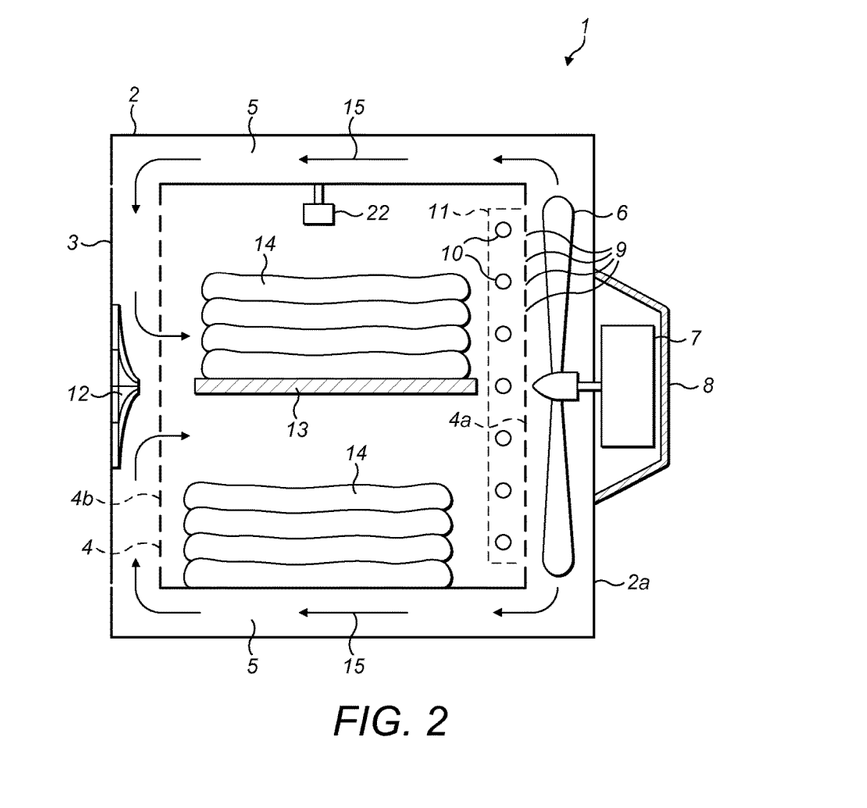
FIG. 2 shows a cross-sectional view along the line X-X of the garment sanitizer of FIG. 1.

FIG. 2 shows a cross-sectional view of the garment sanitizer 1 along the line X-X as shown in FIG. 1 and shows the garment sanitizer 1 comprises a chamber 4 within the housing 2, the chamber 4 defined by a plurality of outer walls which are spaced from the outer panels of the housing. Air flow passages 5 are thereby formed in the spaces between the housing panels and the chamber walls.

A fan 6 is provided between a first wall 4a of the chamber 4, which in the embodiment shown comprises a rear wall of the chamber 4, and the rear panel 2a of the housing 2, and is driven by an electric motor 7 provided on the outside of the housing 2 within a protective covering 8. It should be appreciated however, that the electric motor 7 may alternatively be provided inside the housing 2 within the scope of the invention.

The first wall 4a of the chamber 4 includes a plurality of holes 9 to allow air to flow therethrough. A heater 10 is provided on the first wall 4a of the chamber, and may be covered by a protective mesh 11. The heater 10 may comprise a single heating element which extends back and forth snaking across the first wall 4a of the chamber 4, as shown in FIG. 1. The heating element may be electrically powered.

A second wall 4b of the chamber, which in the embodiment shown comprises a front wall of the chamber 4, comprises a mesh to allow air to freely flow therethrough, and is hinged to allow access to the interior of the chamber 4. The door 3 of the housing 2 includes an airflow guide 12 having a plurality of vanes configured to guide heated air flowing from the air flow passages 5 around the outside of the chamber 4 that then converges at the front door 3 of the housing 2, into the front of the chamber 4 through the second wall 4b of the chamber 4. The airflow guide 12 is generally circular and formed in a spiral starfish configuration. The chamber 4 includes at least one shelf 13 to support one or more garments 14 within the chamber 4.

In use, the door 3 and second wall 4b of the chamber 4 are opened and garments 14 are placed in the chamber 4, either on the bottom wall of the chamber 4 or on the shelf 13. The door 3 and second wall 4b of the chamber 4 are then closed. The garment sanitizer 1 is then connected to a power supply (not shown) and switched on, and the fan 6 and heater 10 are powered. The fan 6 draws air through the chamber 4 and over the heater 10 which heats the air. The air is then drawn through the holes 9 in the first wall 4a of the chamber 4 and is driven radially outwards and flows through the airflow passages 5 around the outside of the chamber 4 towards the front of the housing 2, as shown in FIG. 2 by airflow indicator arrows 15. When the airflow meets the front panel of the housing 2, it is deflected towards the center of the door 3 where it meets the airflow guide 12 which guides the airflow back into the chamber 4 through the mesh of the chamber second wall 4b.

The circulating hot air passes around and permeates the garments 14 and heats the garments 14. In addition to hot air circulation through the chamber 4, the garments 14 are also heated directly by radiation from the heater 10, and the circulating airflow helps to maintain an even temperature throughout the garments 14. The combined radiation and hot air circulation heating effects heat the garments 14 to a temperature sufficient to kill any germs and bacteria that may be present, thereby sanitizing the garments 14. Advantageously, the hot air heats the garments from one side, namely the front of the chamber 4, and the radiation from the heater 10 heats the garments from the opposite side, namely the rear of the chamber 4. This heating from opposite sides of the chamber 4 provides quick and even heating of the garments 14 and therefore a quicker thorough garment sanitizing process.

The vanes of the airflow guide 12 may be curved or otherwise shaped so as to provide turbulence in the hot air flow passing through the chamber 4. This ensures a thoroughly mixed airflow through the chamber 4 for effective heat transfer to the garments 14.

The garment sanitizer 1 may include a control system 16, 19 to control its operation. The control system 16, 19 includes a user interface in the form of a control unit 16 (see FIG. 1) for a user to control operation of the garment sanitizer 1. The control unit 16 may include a display 17 and one or more control buttons 18. The control system additionally includes a controller 19 connected to the control unit 16, which is shown schematically in FIG. 3. The controller 19 comprises a processor 20 and a memory unit 21. The controller 19 is configured to receive input command signals from the control buttons 18 of the control unit 16, and to output a display signal to the display 17 of the control unit 16. The memory unit 21 may include one or more pre-set operation programs for operation of the garment sanitizer 1, for example, a single-garment program, a multi-garment program, and different programs for different garment materials. Each program may have different parameters, for example, the single-garment program may be shorter than the multi-garment program, and a program for cotton garments may run at a higher temperature than a program for wool garments or other "delicate" garments.

Figure 3:
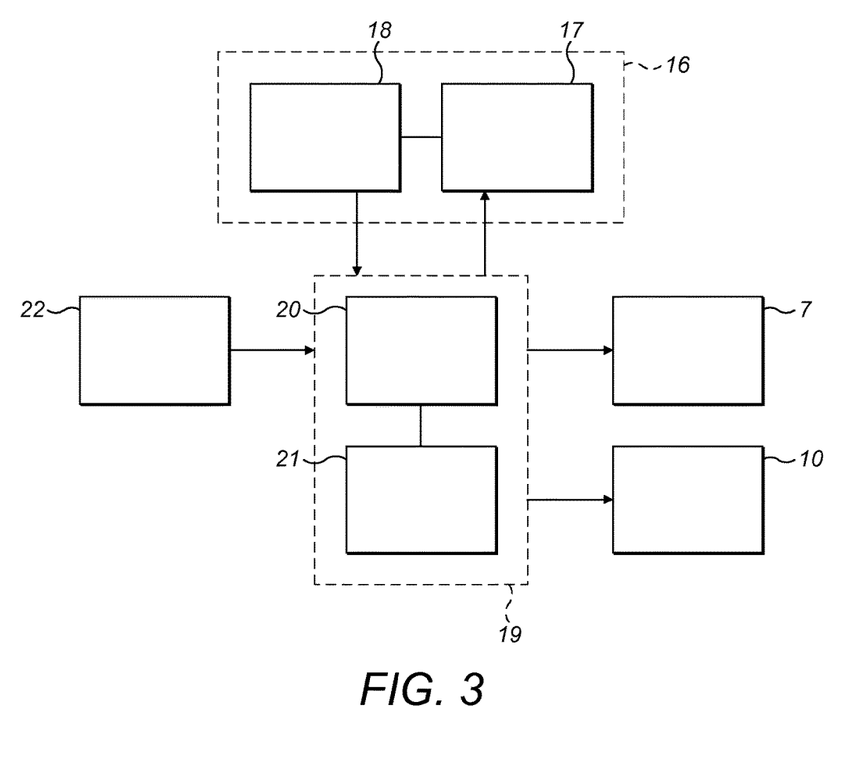
FIG. 3 shows a schematic view of a control system of the garment sanitizer of FIGS. 1 and 2.

The controller 19 is also connected to the motor 7 that drives the fan 6, and the heater 10 so as to control operation of both. Preferably, the garment sanitizer 1 also includes a temperature sensor 22 within the chamber 4 which is connected to the controller 19 so that the controller 19 can receive a temperature signal from the temperature sensor 22 representing the detected temperature within the chamber 4.

A user may operate the garment sanitizer 1 using the control unit 16 to select a desired garment sanitizing program. The controller 19 would then control operation of the heater 10 and fan 6 in dependence on the program selected. During operation, the temperature sensor 22 sends temperature signals to the controller 19. If the detected temperature within the chamber 4 exceeds the desired operating temperature of the selected program, or is outside a permitted tolerance of the desired operating temperature, the controller 19 may turn off the heater 10, or reduce power supply to the heater 10, until the detected temperature falls to the desired operating temperature or within a permitted range of tolerance of the desired temperature. Also, the controller 19 may include a timer so that it can operate the garment sanitizer 1 for a predetermined period of time in dependence on the selected operating program, and to stop operation of the garment sanitizer 1 when the program concludes after the predetermined operating time has elapsed.

Figure 4:
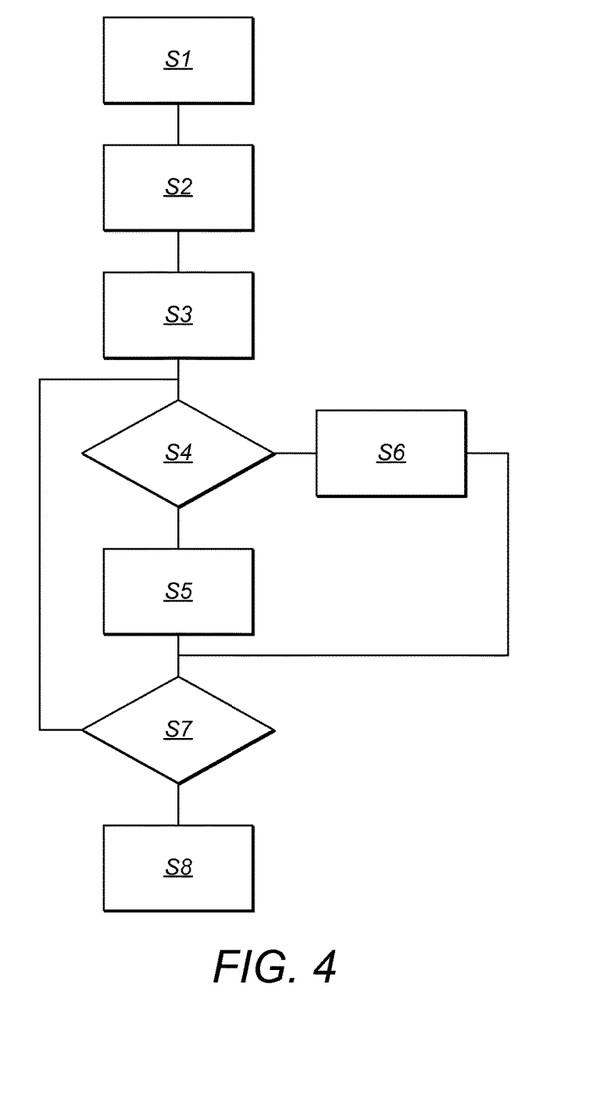
FIG. 4 shows a flow diagram of an example operation process of the garment sanitizer of FIGS. 1 and 2.

An exemplary operation process of the garment sanitizing device 1 of the invention is shown schematically in the flow chart of FIG. 4. At step S1, the garment sanitizing process is started via a user selecting the desired program on the user interface 18 of the control unit 16. At step S2, the controller 19 sets the timer count to zero and begins the process timer. At step S3, the electric motor 7 is powered to operate the fan 6. At step S4, the controller 19 uses the temperature signal from the temperature sensor 22 to query whether the temperature within the chamber 4 is greater than a predetermined maximum threshold temperature for the selected sanitizing process. If the temperature is not above the maximum threshold temperature, the heater 10 is powered at step S5 and the process proceeds to step S7. If the temperature is above the maximum threshold temperature, power to the heater 10 is stopped and the process proceeds to step S7. At step S7, the controller 19 queries whether the elapsed time since the start of the process has reached the pre-set cycle duration time. If the pre-set cycle duration time has not been reached, the process loops back to step S4. If the pre-set cycle duration time has elapsed, the sanitization process is complete and so the process proceeds to step S8 which is the end of the process.

The controller 19 may execute a safety shut-off function for the garment sanitizer 1, by monitoring the temperature within the chamber 4 during operation of the garment sanitizer 1 using the temperature sensor 22, and automatically stopping operation of the garment sanitizer 1 if the detected temperature exceeds a maximum threshold safety temperature. Alternatively, as described above, the controller may shut off power to the heater 10 but maintain operation of the fan until the detected temperature falls to a predetermined level, or within a predetermined temperature range.

One of the pre-set operation programs stored in the memory unit 21 of the processor 19 may comprise a "self-clean" program intended to kill any bacteria within the garment sanitizer 1 whilst no garments are within the chamber 4. Such a program may comprise the garment sanitizer operating for a short time at a high-temperature.

Figure 5:
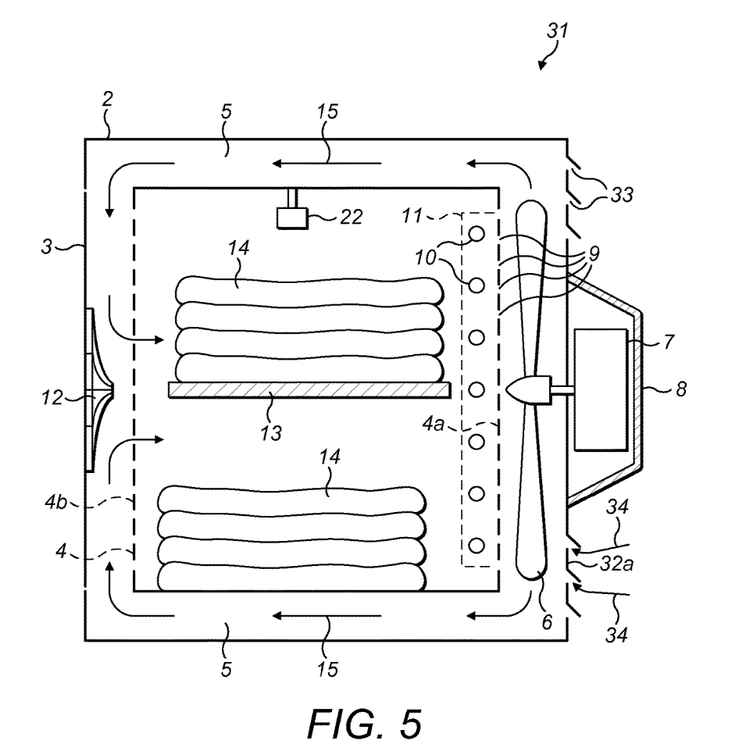
FIG. 5 shows a cross-sectional view of a garment sanitizer of a second embodiment of the invention.

A garment sanitizer 31 of a second embodiment of the invention is shown in FIG. 5 and is similar to the garment sanitizer 1 of the first embodiment, and like features retain the same reference numerals and so detailed description of these features will not be repeated. A difference between the garment sanitizer 31 of a second embodiment is that it provides an open air circulation system whereas the garment sanitizer 1 of the first embodiment provides a closed circulation system. That is, when the door 3 of the garment sanitizer 1 of the first embodiment is closed, only air within the housing 2 can be circulated within the chamber 4 and air flow passages 5. However, the rear panel 32a of the housing 2 of the second embodiment includes a plurality of open vents 33 which allow ambient air to be drawn into the housing 2 when the fan 6 is in operation, as shown by arrows 34. This ambient air is then driven radially outwards by the fan 6 and continues through the air flow passages 5 and into the chamber 4, and then passes over the heater 10 and is heated, and continues to be circulated through the chamber 4 as described previously with reference to the garment sanitizer 1 of the first embodiment. The fan 6 will generally keep the hot air circulating within the garment sanitizer 31 without a large proportion of the heated air escaping back out of the vents 33. However, there will be a certain amount of hot air that escapes out of the vents 33, although this will be replaced by more ambient air being drawn into the garment sanitizer 31 as described above. This embodiment advantageously allows a continual replacement of the circulating air within the garment sanitizer 31 and thereby ensures fresh air is always circulating.

Although the garment sanitizers 1, 31 of the first and second embodiments are shown and described above as having a chamber second wall 4b as a mesh, the invention is not intended to be limited to such a configuration and the chamber may omit a second wall at the front of the chamber within the scope of the invention.

The garment sanitizers 1, 31 of the first and second embodiments are shown and described above as having a single heater 10 which both radiates the garments 14 and also heats the circulating air. However, the invention is not intended to be limited to such a configuration and an alternative embodiment of a garment sanitizer of the invention (not shown) may include one or more heaters to heat the garments by radiation and one or more additional separate heaters to heat the air circulating within the garment sanitizer.

Although the garment sanitizers 1, 31 of the first and second embodiments are shown and described above as having a heater 10 disposed within the chamber 4, the invention is not intended to be limited to such a configuration and the heater may alternatively be disposed between the chamber walls and housing panels within the scope of the invention.

Although the garment sanitizers 1, 31 of the first and second embodiments are shown and described as having the fan 6 and heater 10 disposed at the rear of the appliance, so that the air flow passes from the front to the rear within the chamber 4, the invention is not intended to be limited to such an embodiment, and in an alternative embodiment of the invention (not illustrated), the fan 6, and possibly also the heater 10, may be mounted on the front of the appliance, such as on the door 3, so that the air flow passes from the rear to the front within the chamber 4, or may still pass from the front to the rear within the chamber 4, depending on the configuration of fan and/or heater of such an alternative embodiment. Furthermore, the fan and heater may be disposed at one side of the appliance such that the air flow is directed through the chamber 4 from one side to the opposite side. In such an embodiment, the air flow guide 12 would be disposed on the inside of the side panel of the housing 2 opposite to the side at which the fan 6 and heater 10 are disposed, to guide the air flow back into the chamber 4, rather than being disposed on the door 3. Also, the side walls of the chamber 4 would be formed as a mesh or open to allow the circulation of airflow through the chamber 4.

Although in the garment sanitizers 1, 31 of the first and second embodiments the heater 10 is shown as heating elements over which air is conveyed to be heated, the invention is not intended to be limited to such an embodiment and other configurations of heaters may be used, such that air may be conveyed via, past, through or otherwise interact with the heating element to heat the air.

Although in the garment sanitizers 1, 31 of the first and second embodiments the control unit 16 is mounted on a side panel of the housing 2, the invention is not intended to be limited to such a configuration and in an alternative embodiment (not illustrated), the control unit 16 may be mounted on the door 3, top surface, or any other surface of the appliance. Yet further, it is intended within the scope of the invention that the control unit 16 may comprise a remote control unit not connected to the appliance and which is configured to control operation of the appliance remotely, for example, via an infra-red controller, or other remote control signal device. Also, the appliance may be configured to be controlled by a mobile phone using an appropriate app on the phone and the phone remotely linked or otherwise able to control the appliance.

Although in the garment sanitizers 1, 31 of the first and second embodiments show a temperature sensor 22 within the chamber, the invention is not intended to be limited to such a sensor, and in alternative embodiments within the scope of the invention, one or more additional or alternative sensors may be provided, including but not limited to an airflow sensor to detect airflow rate or speed within the chamber, a height sensor to detect the height of garments stacked within the chamber, and a weight sensor to detect the weight of garments stacked within the chamber. Details and advantages of such alternative embodiments of the invention are as described above. Yet further, the sensor may be mounted between the walls of the chamber and the housing panels, rather than within the chamber as shown in FIGS. 2 and 5. This may enable detection of the relevant parameters from airflow between the chamber walls and housing panels, unobstructed by any garments within the chamber.

It will be appreciated that the term "comprising" does not exclude other elements or steps and that the indefinite article "a" or "an" does not exclude a plurality. A single processor may fulfil the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalization thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A garment sanitizing device comprising:
    a housing comprising a plurality of panels,
    a single chamber within the housing comprising a plurality of walls to receive one or more garments to be sanitized,
    the chamber comprising a bottom wall, a top wall, and opposite first and second sides each extending from the bottom wall to the top wall, wherein one of the first and second sides of the chamber are hinged to allow access to the interior of the chamber,
    the housing containing a fan and one or more heating elements,
    wherein the fan is disposed in a space between a rear panel of the housing and one of said first and second sides of the chamber
    wherein the at least one heating element is disposed proximate the first side of the chamber to heat garments within the chamber from the first side of the chamber by radiation,
    wherein the second side of the chamber includes an air inlet,
    wherein the fan is configured to convey air via the at least one heating element to heat the air and to convey the heated air into the chamber through the air inlet in the second side of the chamber to additionally heat the garments by the conveyed heated air.

2. A garment sanitizing device according to claim 1 comprising at least one air flow passage configured to guide the flow of heated air from the fan.

3. A garment sanitizing device according to claim 2 wherein the chamber comprises a plurality of walls and the housing comprises a plurality of panels, and the chamber is disposed within the housing such that the chamber walls are spaced from the housing panels such that at least one air flow passage is defined between the chamber walls and the housing panels, and the garment sanitizing device is configured such that air is circulated by the fan from the chamber, through the air flow passage and back into the chamber.

4. A garment sanitizing device according to claim 3 further comprising an airflow guide to guide air from the air flow passage into the chamber.

5. A garment sanitizing device according to claim 4 wherein the airflow guide projects from proximate a central portion of a panel of the housing.

6. A garment sanitizing device according to claim 2 wherein the chamber includes a first wall on the first side of the chamber which comprises a plurality of apertures though which air may pass when being circulated by the fan.

7. A garment sanitizing device according to claim 6 wherein the chamber includes a second wall on the second side of the chamber opposite to the first side, and wherein the second wall includes a plurality of apertures through which air may pass when being circulated by the fan.

8. A garment sanitizing device according to claim 1 wherein at least one shelf is provided within the chamber to receive garments to be sanitized, and wherein the garment sanitizing device is configured to convey the heated air through the chamber and over the shelf in a direction parallel to the plane of the shelf.

9. A garment sanitizing device according to claim 1 comprising a single heating element configured to heat garments within the chamber by radiation and also configured to heat air conveyed through the chamber by the fan.

10. A garment sanitizing device according to claim 1 further comprising a control system configured to control its operation, and one or more sensors connected to the control system and configured to detect one or more parameters within the garment sanitizing device and/or the chamber, and operation of the garment sanitizing device is controlled in dependence upon signals received from the sensor(s).

11. A garment sanitizing device according to claim 10 wherein the sensor comprises a temperature sensor, and the control system is configured to control the garment sanitizing device to operate within a temperature range within the chamber of between 50 to 120 degrees Celsius.

12. A garment sanitizing device according to claim 10 comprising a height sensor configured to determine the height of a stack of garments within the chamber, wherein the control system is configured to control the fan speed in dependence on the signal(s) received from the height sensor.

13. A garment sanitizing device according to claim 1, wherein the housing includes a front door on one of said plurality of panels, said front door including an airflow guide having a plurality of vanes configured to guide heated air flowing from air flow passages around the outside of the chamber to converge at the front door of the housing into the front of the chamber through the second wall of the chamber.

14. A garment sanitizing device according to claim 1, wherein said opposite first and second sides of the chamber include a plurality of apertures effectively comprising a mesh through which air may pass when being circulated by the fan.

15. A method of sanitizing a garment using a garment sanitizing device comprising a housing, a chamber within the housing to receive one or more garments to be sanitized, the chamber comprising a bottom wall, a top wall, and opposite first and second sides each extending from the bottom wall to the top wall, the housing containing a fan and one or more heating elements, the at least one heating element being disposed proximate the first side of the chamber and an air inlet disposed at the second side of the chamber, the method comprising, placing garments within the chamber, directly heating the garments within the chamber from the first side of the chamber by radiation from the at least one heating element, and additionally heating the garments using heated air by activating the fan to convey air via the at least one heating element to heat the air and to convey the heated air through the chamber from the air inlet in the second side of the chamber via air flow passages around an outside of the chamber to converge at a front of the housing towards a front of the chamber to pass through the second side of the chamber to heat the garments.

* * * * *